United States Patent
Pfeil et al.

(10) Patent No.: US 6,752,928 B2
(45) Date of Patent: Jun. 22, 2004

(54) FLOW MATCHING METHOD AND SYSTEM USING TWO TRANSDUCERS

(75) Inventors: Michael C. Pfeil, Dayton, OH (US); Gary C. Fulks, Spring Valley, OH (US)

(73) Assignee: Delphi Technologies, Inc., Troy, MI (US)

( * ) Notice: Subject to any disclaimer, the term of this patent is extended or adjusted under 35 U.S.C. 154(b) by 172 days.

(21) Appl. No.: 10/045,776

(22) Filed: Jan. 10, 2002

(65) Prior Publication Data

US 2003/0130608 A1 Jul. 10, 2003

(51) Int. Cl.$^7$ .............................. B01D 61/32; F17D 3/00
(52) U.S. Cl. ...................... 210/646; 137/10; 210/137; 210/321.65; 210/929; 604/65
(58) Field of Search ........................ 210/85, 87, 96.2, 210/97, 103, 137, 321.71, 637, 646, 739, 929; 73/1.01, 1.02, 1.16, 1.35, 861, 196, 861.42; 137/2, 8, 98, 100, 101.19, 565.11; 604/4.01, 5.01, 65, 67

(56) References Cited

U.S. PATENT DOCUMENTS

| | | | | |
|---|---|---|---|---|
| 4,021,341 A | * | 5/1977 | Cosentino et al. | ............ 210/87 |
| 4,132,644 A | * | 1/1979 | Kolberg | ........................ 210/85 |
| 4,370,983 A | * | 2/1983 | Lichtenstein | ................ 600/301 |
| 5,111,683 A | | 5/1992 | Fond | |
| 5,399,157 A | | 3/1995 | Goux et al. | |
| 5,455,781 A | | 10/1995 | Reynal et al. | |
| 5,975,353 A | | 11/1999 | Finlayson | |
| 6,280,632 B1 | * | 8/2001 | Polaschegg | ................. 210/739 |
| 6,509,113 B2 | | 1/2003 | Keegan | |
| 6,607,069 B2 | * | 8/2003 | Tonnigs et al. | .......... 198/465.1 |
| 6,610,027 B1 | * | 8/2003 | El Hatu | ....................... 604/65 |
| 6,613,469 B2 | | 9/2003 | Keegan | |

FOREIGN PATENT DOCUMENTS

| | | |
|---|---|---|
| EP | 0 806 718 A | 11/1997 |
| GB | 1353197 | 5/1974 |

OTHER PUBLICATIONS

International Search Report of EP Patent Application No. 02080350.8 dated Mar. 28, 2003.

* cited by examiner

*Primary Examiner*—Joseph Drodge
(74) *Attorney, Agent, or Firm*—Scott A. McBain

(57) ABSTRACT

A property of unconnected first and second fluid flows is matched, such as, but not limited to, matching the flow rate of the replacement water stream with the waste water stream in kidney dialysis. The first and second flow paths are interconnected so substantially the same flow from the first flow source encounters a first flow transducer which is in the first flow path and a second flow transducer which is in the second flow path. Transducer readings are taken for various identical values of the property of the first fluid flow. Then the first and second flow paths are disconnected, and the property, such as but not limited to flow rate, of one of the fluid flows in one of the flow paths is controlled using transducer readings and the previous interconnected-path transducer readings to match the property in the two flows. In one example, the transducers are uncalibrated transducers.

19 Claims, 3 Drawing Sheets

FLOW MATCHING METHOD AND SYSTEM USING TWO TRANSDUCERS

TECHNICAL FIELD

The present invention relates generally to fluid flow, and more particularly to a flow matching method and system using two transducers.

BACKGROUND OF THE INVENTION

Certain procedures require the matching of two fluid flows. Conventional flow matching systems use a finely calibrated flow rate transducer to measure the flow rate in the first flow path and use another finely calibrated flow rate transducer to measure the flow rate in the second flow path. A valve in the first flow path is controlled such that the reading of the finely calibrated flow rate transducer in the first flow path matches the reading of the finely calibrated flow rate transducer in the second flow path.

What is needed is an improved method for matching first and second flows and an improved fluid flow matching system useful, for example, in performing kidney dialysis.

SUMMARY OF THE INVENTION

A first method of the invention is for matching the flow rate of first and second fluid flows in respective, fluidly-unconnected first and second flow paths, wherein the first flow path includes a first flow source and a first flow-rate transducer, and wherein the second flow path includes a second flow source and a second flow-rate transducer. The first method includes steps a) through g). Step a) includes shutting off the second flow source. Step b) includes fluidly interconnecting the first and second flow paths creating an interconnected flow path which allows substantially the same flow from the first flow source to encounter the first and second flow-rate transducers. Step c) includes, after steps a) and b), obtaining readings from the first and second flow-rate transducers for various identical values of the flow rate of the first flow source. Step d) includes, after step c), disconnecting the fluid interconnection between the first and second flow paths. Step e) includes turning on the second flow source. Step f) includes, after steps d) and e), obtaining a reading from the first flow-rate transducer and a reading from the second flow-rate transducer. Step g) includes controlling the flow rate of the first fluid flow to match the flow rate of the second fluid flow using the readings from step f) and using the readings in step c).

A second method of the invention is for matching a property of first and second fluid flows in respective, fluidly-unconnected first and second flow paths, wherein the first flow path includes a first flow source and a first flow transducer which measures the property, and wherein the second flow path includes a second flow source and a second flow transducer which measures the property. The second method includes steps a) through g). Step a) includes shutting off the second flow source. Step b) includes fluidly interconnecting the first and second flow paths creating an interconnected flow path which allows substantially the same flow from the first flow source to encounter the first and second flow transducers. Step c) includes, after steps a) and b), obtaining readings from the first and flow transducers for various identical values of the property of the first flow source. Step d) includes, after step c), disconnecting the fluid interconnection between the first and second flow paths. Step e) includes turning on the second flow source. Step f) includes, after steps d) and e), obtaining a reading from the first flow transducer and a reading from the second flow transducer. Step g) includes controlling the fluid flow in one of the first and second flow paths to match the property of the first and second fluid flows using the readings from step f) and using the readings in step c).

In a first expression of an embodiment of the invention, a fluid flow matching system includes a first fluid flow path, a second fluid flow path, a fluid interconnection path, and data. The first fluid flow path has a servo-controlled actuator which controls a property of the first fluid flow and has in series a first flow source, a first flow transducer, and a first valve. The second fluid flow path has in series a second valve and a second flow transducer. The fluid interconnection path has in series a first end, an interconnection valve, and a second end. The first end is in fluid communication with the first fluid flow path between the first valve and the first flow transducer. The second end is in fluid communication with the second fluid flow path between the second valve and the second flow transducer. The data represent readings of the first and second flow transducers for various identical values of the property of the first flow source taken with the first valve fully shut, the interconnection valve fully open, and the second valve fully shut. The servo-controlled actuator is controlled from readings of the first and second flow transducers taken with the first valve fully open, the interconnection valve fully shut, and the second valve fully open and from the data.

In a second expression of an embodiment of the invention, a fluid flow-rate matching system includes a first fluid flow path, a second fluid flow path, a fluid interconnection path, and data. The first fluid flow path has in series a first flow source, a servo-controlled valve, a first flow-rate transducer, and a first valve. The second fluid flow path has in series a second valve and a second flow-rate transducer. The fluid interconnection path has in series a first end, an interconnection valve, and a second end. The first end is in fluid communication with the first fluid flow path between the first valve and the first flow-rate transducer. The second end is in fluid communication with the second fluid flow path between the second valve and the second flow-rate transducer. The data represent readings of the first and second flow-rate transducers for various identical values of the flow rate of the first flow source taken with the first valve fully shut, the interconnection valve fully open, and the second valve fully shut. The servo-controlled valve is controlled from readings of the first and second flow-rate transducers taken with the first valve fully open, the interconnection valve fully shut, and the second valve fully open and from the data.

Several benefits and advantages are derived from one or more of the methods and/or expressions of the embodiment of the invention. The matching of one fluid flow to another fluid flow, such as matching the flow rate of the replacement water stream to the flow rate of the waste water stream in kidney dialysis, is accomplished without having to use calibrated flow transducers. Using uncalibrated flow transducers reduces costs.

DESCRIPTION OF THE PREFERRED EMBODIMENT

Figure 1:
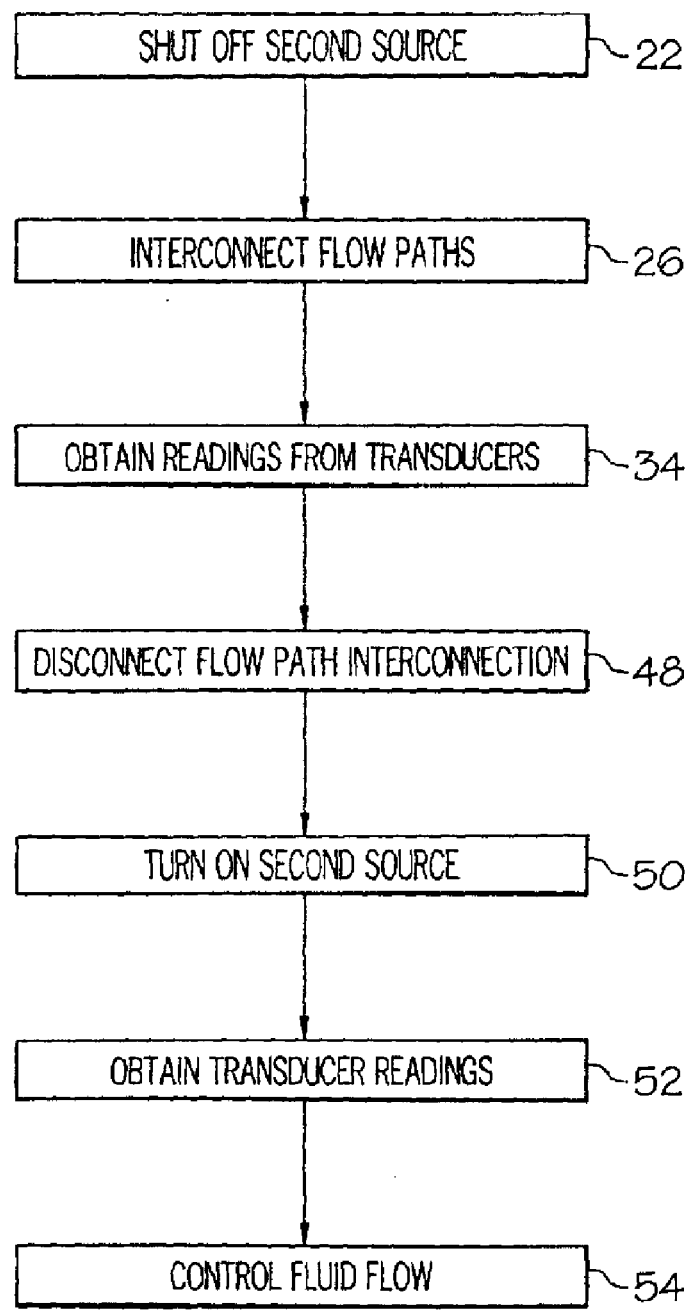
FIG. 1 is a flow chart of a method for matching first and second fluid flows in respective, fluidly-unconnected first and second flow paths.
Figure 2:
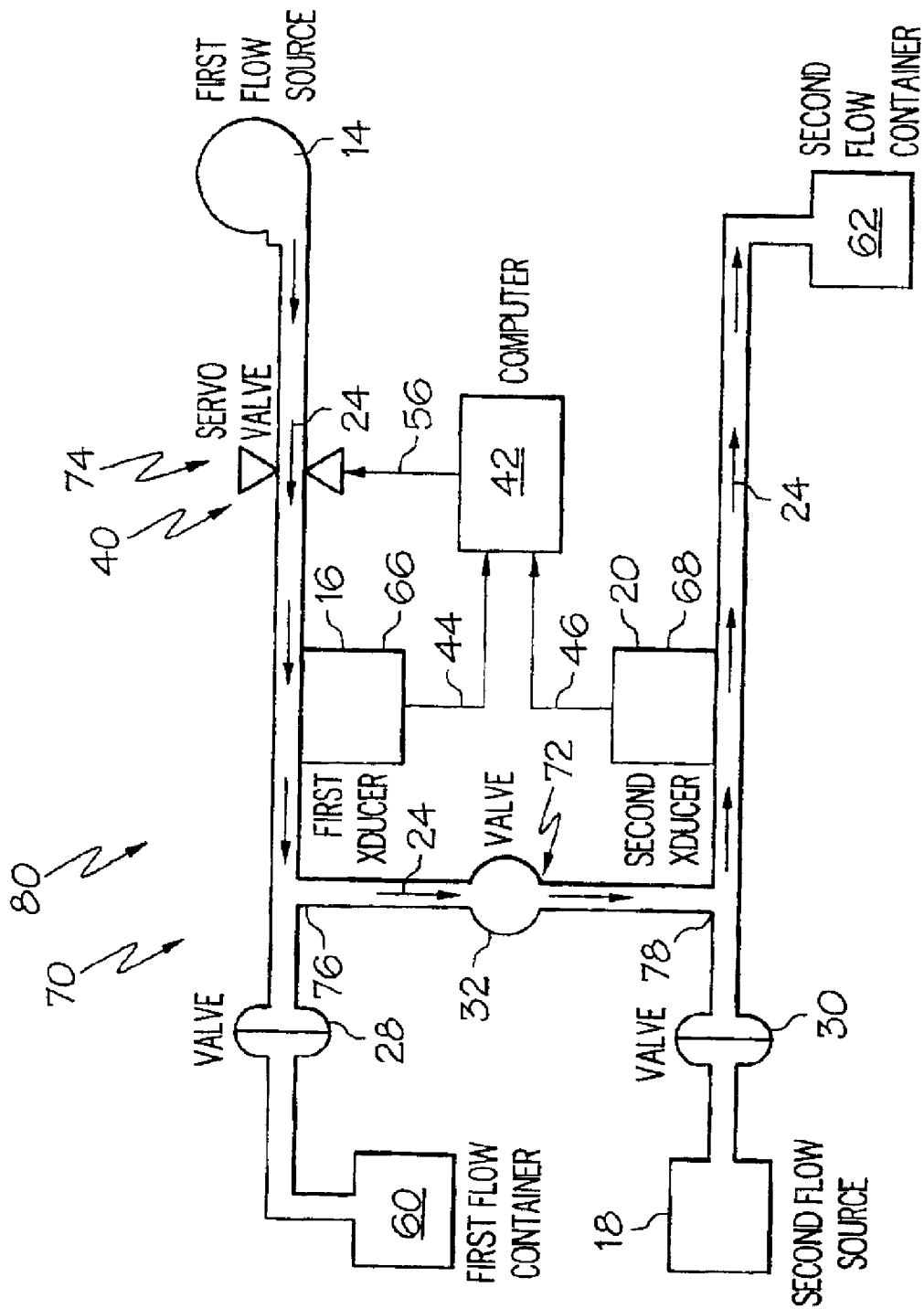
FIG. 2 is a schematic diagram of an embodiment of apparatus for carrying out the method of FIG. 1 shown in an analysis mode wherein the flow paths are interconnected to obtain transducer readings for the same flow.
Figure 3:
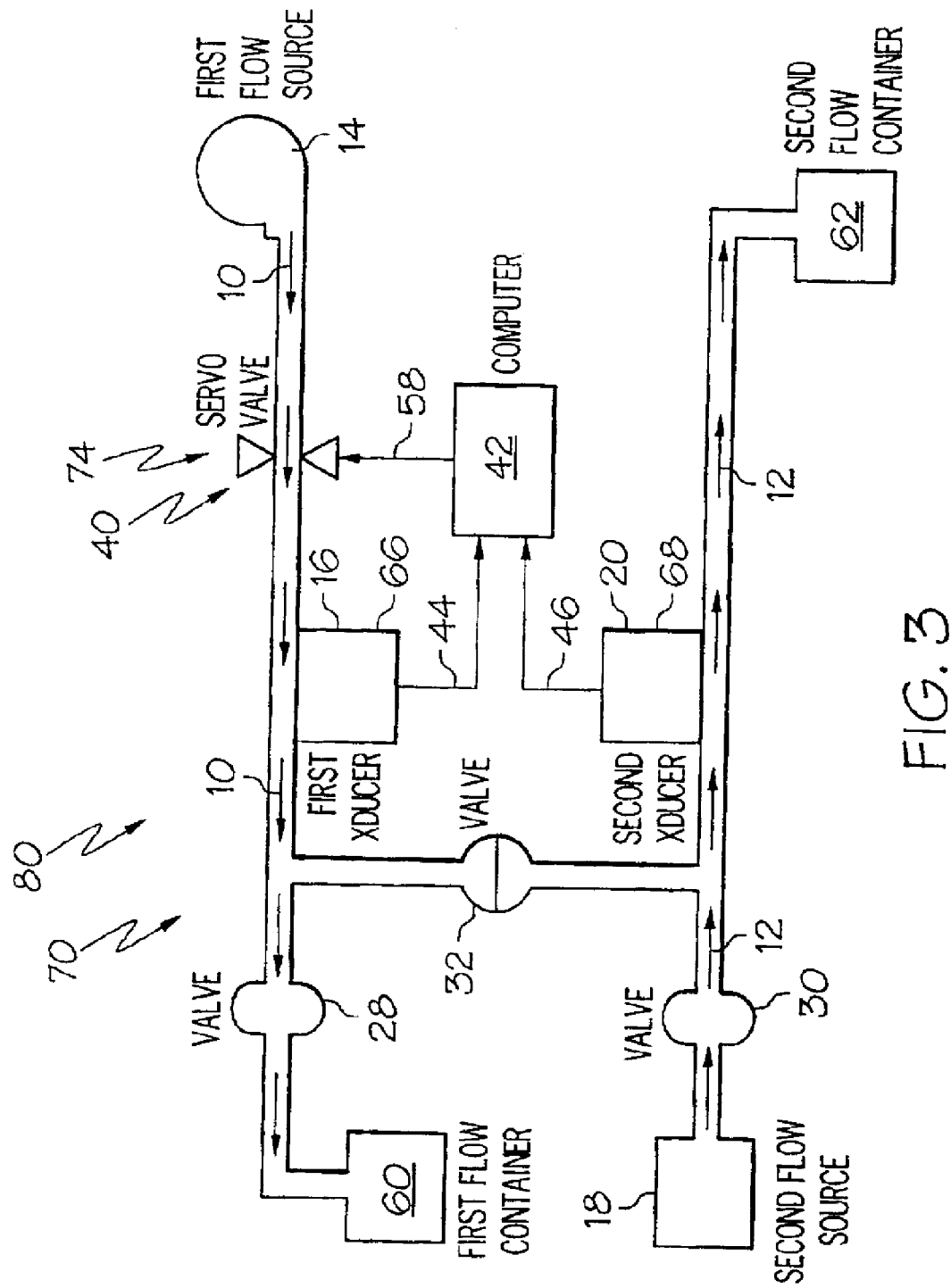
FIG. 3 is a view as in FIG. 2 but with the apparatus shown in a control mode wherein the flow paths are unconnected for matching the first and second flows using transducer readings and using the previous transducer readings obtained from the analysis mode of FIG. 2.

Referring now to the drawings, wherein like numerals represent like elements throughout, FIG. 1 shows a first method of the invention, and FIGS. 2 and 3 show an embodiment of apparatus for carrying out the first method. The first method is for matching the flow rate of first and second fluid flows in respective, fluidly-unconnected first and second flow paths 10 and 12 (shown by flow arrows in FIG. 3 and also called fluid flow paths), wherein the first flow path 10 includes a first flow source 14 and a first flow-rate transducer 16, and wherein the second flow path 12 includes a second flow source 18 and a second flow-rate transducer 20. The first method includes steps a) through g).

Step a) is labeled as "Shut Off Second Source" in block 22 of FIG. 1. Step a) includes shutting off the second flow source 18. In one implementation of step a), the second flow source is powered down. In another implementation of step a), a closed valve is used to isolate the second flow source.

Step b) is labeled as "Interconnect Flow Paths" in block 26 of FIG. 1. Step b) includes fluidly interconnecting the first and second flow paths creating an interconnected flow path 24 (shown by flow arrows in FIG. 2) which allows substantially the same flow from the first flow source 14 to encounter the first and second flow-rate transducers 16 and 20. In an overlapping implementation of steps a) and b), as shown in FIG. 2, the first and second valves 28 and 30 are fully shut and the interconnection valve 32 is fully open.

Step c) is labeled as "Obtain Readings From Transducers" in block 34 of FIG. 1. Step c) includes, after steps a) and b), obtaining readings from the first and second flow-rate transducers 16 and 20 for various identical values of the flow rate of the first flow source 14. The identical value of the flow rate need not be a known value but it must be substantially the identical value. In one implementation of step c), the servo-controlled valve 40 in FIG. 2 is incrementally closed (or opened) to create the various identical values of the flow rate from the first flow source 14, and the flow is allowed to reach steady state before the transducer readings are taken. Other implementations of step c) are left to the artisan. In one application of the first method, step c) includes storing the transducer readings in a map file in a computer 42 with the first flow-rate transducer 16 sending its reading to the computer 42 through signal 44 and with the second flow-rate transducer 20 sending its reading to the computer through signal 46. In one variation, the map file is a two column file, wherein the first column is viewed as the adjusted readings of the first flow-rate transducer 16, wherein the second column is the readings of the second flow-rate transducer 20, and wherein the first and second flow-rate transducer readings in the same row of the map file are readings taken for an identical flow rate of the first flow source 14. In one example, the computer 42 incrementally controls the closing (or opening) of the servo-controlled valve 40 through signal 56. Other implementations of step c) are left to the artisan.

Step d) is labeled as "Disconnect Flow Path Interconnection" in block 48 of FIG. 1. Step d) includes, after step c), disconnecting the fluid interconnection between the first and second flow paths.

Step e) is labeled as "Turn On Second Source" in block 50 of FIG. 1. Step e) includes turning on the second flow source 18. In one implementation of step e), the second flow source is powered up. In another implementation of step e), an open valve is used to provide fluid access to the second flow source. In an overlapping implementation of steps d) and e), as shown in FIG. 3, the first and second valves 28 and 30 are fully open and the interconnection valve 32 is fully shut.

Step f) is labeled as "Obtain Transducer Readings" in block 52 of FIG. 1. Step f) includes, after steps d) and e), obtaining a reading from the first flow-rate transducer 16 and a reading from the second flow-rate transducer 20.

Step g) is labeled as "Control Fluid Flow" in block 54 of FIG. 1. Step g) includes controlling the flow rate of the first fluid flow to match the flow rate of the second fluid flow using the readings from step f) and using the readings in step c) [such use of step c) readings including using interpolated and/or extrapolated step c) readings]. As one illustration of one implementation of step g), assume one row of the map file, of the previously described application of step c), has "10" as the value of the first flow-rate transducer reading (the so-called adjusted first flow-rate transducer reading), and has "12" as the value of the second flow-rate transducer reading. Assume that the step g) reading of the first flow rate transducer 16 is "4" and the reading of the second flow rate transducer 20 is "12". The computer 42 looks in the map file for a "12" reading of the second flow rate transducer to obtain an adjusted reading of "10" from the same row (i.e., for the identical flow rate value) of the map file for the first flow rate transducer. The computer 42 then compares the desired or adjusted value of "10" with the actual value of "4" of the first flow-rate transducer reading to obtain an error control signal (i.e., the desired minus the actual value) of "6" to control a valve (e.g., the servo-controlled valve 40) in the first flow path 10 to control the flow rate in the first flow path 10. In one variation, the computer 42 sends the control signal to the servo-controlled valve 40 through signal 58 to obtain closed loop control of the servo-controlled valve 40 to match the flow rate of the first fluid flow to the flow rate of the second fluid flow, as can be appreciated by those skilled in the art. Other implementations of step g) are left to the artisan including, without limitation, using a controllable pump or other controllable flow source in place of the servo-controlled valve 40.

In one example of the first method, the first and second flow-rate transducers 16 and 20 are differential pressure transducers. It is noted that a flow transducer measures a property of a fluid flow if it directly or indirectly measures that property. In one variation, the first and second flow-rate transducers are uncalibrated differential pressure transducers. Other examples of flow-rate transducers are left to the artisan. In one application of the first method, the first flow path 10 is a replacement water flow path of a kidney dialysis machine, and the second flow path 12 is a waste water flow path of the kidney dialysis machine. In this application, the first flow container 60 represents the joining of the first fluid flow (here the replacement water stream) and the thickened blood stream (not shown) for return to the patient (not shown), and the second flow container 62 represents a waste container. Other applications are left to the artisan.

As can be appreciated by the artisan, a broader and second method of the invention is for matching a property of first and second fluid flows in respective, fluidly-unconnected first and second flow paths 10 and 12, wherein the first flow path 10 includes a first flow source 14 and a first flow transducer 66 which measures the property, wherein the second flow path 12 includes a second flow source 18 and a second flow transducer 68 which measures the property. The second method includes steps a) through g).

Step a) includes shutting off the second flow source 18. Step b) includes fluidly interconnecting the first and second flow paths 10 and 12 creating an interconnected flow path 24 which allows substantially the same flow from the first flow source 14 to encounter the first and second flow transducers 66 and 68. Step c) includes, after steps a) and b), obtaining readings from the first and second flow transducers 66 and 68 for various identical values of the property of the first flow source 14.

Step d) includes, after step c), disconnecting the fluid interconnection between the first and second flow paths 10 and 12. Step e) includes turning on the second flow source 18. Step f) includes, after steps d) and e), obtaining a reading from the first flow transducer 66 and a reading from the second flow transducer 68. Step g) includes controlling the fluid flow in one of the first and second flow paths 10 and 12 to match the property of the first and second fluid flows using the readings from step f) and using the readings in step c).

In one example, the first and second flow transducers 66 and 68 are uncalibrated flow transducers. In one application, step g) matches the property of the first fluid flow to the property of the second fluid flow. In another application, step g) matches the property of the second fluid flow to the property of the first fluid flow. In one implementation of the second method, the property is flow rate, and the first and second flow transducers are flow-rate transducers. Matching of other properties of fluid flows includes, without limitation, matching the temperature, color, or viscosity of a fluid flow. For example, a servo-controlled actuator could be used to regulate the amount of heat to be imparted to the flow, the amount of color dye entering the flow, or the amount of a viscous agent to be added to the flow. Further properties for matching are left to the artisan.

In a first expression of an embodiment of the invention, a fluid flow matching system 70 includes a first fluid flow path 10, a second fluid flow path 12, a fluid interconnection path 72, and data. The first fluid flow path 10 has a servo-controlled actuator 74 which controls a property of the first fluid flow and has in series a first flow source 14, a first flow transducer 66, and a first valve 28. The second fluid flow path 12 has in series a second valve 30 and a second flow transducer 68. The fluid interconnection path 72 has in series a first end 76, an interconnection valve 32, and a second end 78. The first end 76 is in fluid communication with the first fluid flow path 10 between the first valve 28 and the first flow transducer 66, and the second end 78 is in fluid communication with the second fluid flow path 12 between the second valve 30 and the second flow transducer 68. The data represent readings of the first and second flow transducers 66 and 68 for various identical values of the property of the first flow source 14 taken with the first valve 28 fully shut, the interconnection valve 32 fully open, and the second valve 30 fully shut. The servo-controlled actuator 74 is controlled from readings of the first and second flow transducers 66 and 68 taken with the first valve 28 fully open, the interconnection valve 32 fully shut, and the second valve 30 fully open and from the data. In one example, the data are stored in a map file in a computer 42.

In a second expression of an embodiment of the invention, a fluid flow-rate matching system 80 includes a first fluid flow path 10, a second fluid flow path 12, a fluid interconnection path 72, and data. The first fluid flow path 10 has in series a first flow source 14, a servo-controlled valve 40, a first flow-rate transducer 16 and a first valve 28. The second fluid flow path 12 has in series a second valve 30 and a second flow-rate transducer 20. The fluid interconnection path 72 has in series a first end 76, an interconnection valve 32, and a second end 78. The first end 76 is in fluid communication with the first fluid flow path 10 between the first valve 28 and the first flow-rate transducer 16, and the second end 78 is in fluid communication with the second fluid flow path 12 between the second valve 30 and the second flow-rate transducer 20. The data represent readings of the first and second flow-rate transducers 16 and 20 for various identical values of the flow rate of the first flow source 14 taken with the first valve 28 fully shut, the interconnection valve 32 fully open, and the second valve 30 fully shut. The servo-controlled valve 40 is controlled from readings of the first and second flow-rate transducers 16 and 20 taken with the first valve 28 fully open, the interconnection valve 32 fully shut, and the second valve 30 fully open and from the data. In one example, the data are stored in a computer 42. It is noted that a servo-controlled valve 40 is one type of a servo-controlled actuator 74. Other types of servo-controlled actuators 74 are left to the artisan.

Several benefits and advantages are derived from one or more of the methods and/or expressions of the embodiment of the invention. The matching of one fluid flow to another fluid flow, such as matching the flow rate of the replacement water stream to the flow rate of the waste water stream in kidney dialysis, is accomplished without having to use calibrated flow transducers. Using uncalibrated flow transducers reduces costs.

The foregoing description of several methods and several embodiments of an embodiment of the invention has been presented for purposes of illustration. It is not intended to be exhaustive or to limit the invention to the precise form or procedure disclosed, and obviously many modifications and variations are possible in light of the above teaching. It is intended that the scope of the invention be defined by the claims appended hereto.

What is claimed is:

1. A method for matching a property of first and second fluid flows in respective, fluidly-unconnected first and second flow paths, wherein the first flow path includes a first flow source and a first flow transducer which measures the property, wherein the second flow path includes a second flow source and a second flow transducer which measures the property, and wherein the method comprises the steps of:

a) shutting off the second flow source;

b) fluidly interconnecting the first and second flow paths creating an interconnected flow path which allows substantially the same flow from the first flow source to encounter the first and second flow transducers;

c) after steps a) and b), obtaining readings from the first and second flow transducers for various identical values of the property of the first flow source;

d) after step c), disconnecting the fluid interconnection between the first and second flow paths;

e) turning on the second flow source;

f) after steps d) and e), obtaining a reading from the first flow transducer and a reading from the second flow transducer; and g) controlling the fluid flow in one of the first and second flow paths to match the property of the first and second fluid flows using the readings from step f) and using the readings in step c), wherein the second flow source is independent of the first flow source.

2. The method of claim 1, wherein the first and second flow transducers are uncalibrated flow transducers.

3. The method of claim 1, wherein the property is a flow rate, wherein the first and second flow transducers measure flow rate, and wherein step g) matches the flow rate of the first and second fluid flows.

4. The method of claim 3, wherein the first and second flow transducers are differential pressure transducers.

5. The method of claim 4, wherein the first and second flow transducers are uncalibrated differential pressure transducers.

6. A method for matching the flow rate of first and second fluid flows in respective, fluidly-unconnected first and second flow paths, wherein the first flow path includes a first flow source and a first flow-rate transducer, wherein the second flow path includes a second flow source and a second flow-rate transducer, and wherein the method comprises the steps of:

a) shutting off the second flow source;
   b) fluidly interconnecting the first and second flow paths creating an interconnected flow path which allows substantially the same flow from the first flow source to encounter the first and second flow-rate transducers;
   c) after steps a) and b), obtaining readings from the first and second flow-rate transducers for various identical values of the flow rate of the first flow source;
   d) after step c), disconnecting the fluid interconnection between the first and second flow paths;
   e) turning on the second flow source;
   f) after steps d) and e), obtaining a reading from the first flow-rate transducer and a reading from the second flow-rate transducer; and
   g) controlling the flow rate of the first fluid flow to match the flow rate of the second fluid flow using the readings from step f) and using the readings in step c),
   wherein the second flow source is independent of the first flow source.

7. The method of claim 6, wherein the first and second flow-rate transducers are differential pressure transducers.

8. The method of claim 7, wherein the first and second flow-rate transducers are uncalibrated differential pressure transducers.

9. The method of claim 6, wherein step g) adjusts a valve in the first flow path to control the flow rate in the first flow path.

10. The method of claim 9, wherein the first flow path is a water replacement flow path of a kidney dialysis machine, and wherein the second flow path is a waste water flow path of the kidney dialysis machine.

11. A fluid flow matching system comprising:

a) a first fluid flow path having a servo-controlled actuator which controls a property of the first fluid flow and having in series a first flow source, a first flow transducer, and a first valve;
   b) a second fluid flow path having in series a second flow source, a second valve and a second flow transducer, wherein the second flow source is independent of the first flow source;
   c) a fluid interconnection path having in series a first end, an interconnection valve, and a second end, wherein the first end is in fluid communication with the first fluid flow path between the first valve and the first flow transducer, and wherein the second end is in fluid communication with the second fluid flow path between the second valve and the second flow transducer; and
   d) a computer operable for obtaining data representing readings of the first and second flow transducers for various identical values of the property of the first flow source taken with the first valve fully shut, the interconnection valve fully open, and the second valve fully shut, and controlling the servo-controlled actuator is from readings of the first and second flow transducers taken with the first valve fully open, the interconnection valve fully shut, and the second valve fully open and from the data.

12. The fluid flow matching system of claim 11, wherein the first and second flow transducers are uncalibrated flow transducers.

13. The fluid flow matching system of claim 12, wherein the first and second flow transducers measure flow rate.

14. The fluid flow matching system of claim 13, wherein the first and second flow transducers are differential pressure transducers.

15. The fluid flow matching system of claim 14, wherein the first flow path is a water replacement flow path of a kidney dialysis machine, and wherein the second flow path is a waste water flow path of the kidney dialysis machine.

16. A fluid flow-rate matching system comprising:

a) a first fluid flow path having in series a first flow source, a servo-controlled valve, a first flow-rate transducer, and a first valve;
   b) a second fluid flow path having in series a second flow source, a second valve and a second flow-rate transducer, wherein the second flow source is independent of the first flow source;
   c) a fluid interconnection path having in series a first end, an interconnection valve, and a second end, wherein the first end is in fluid communication with the first fluid flow path between the first valve and the first flow-rate transducer, and wherein the second end is in fluid communication with the second fluid flow path between the second valve and the second flow-rate transducer; and
   d) a computer operable for obtaining data representing readings of the first and second flow-rate transducers for various identical values of the flow rate of the first flow source taken with the first valve fully shut, the interconnection valve fully open, and the second valve fully shut, and controlling the servo-controlled valve is from readings of the first and second flow-rate transducers taken with the first valve fully open, the interconnection valve fully shut, and the second valve fully open and from the data.

17. The fluid flow-rate matching system of claim 16, wherein the first and second flow-rate transducers are uncalibrated flow-rate transducers.

18. The fluid flow-rate matching system of claim 17, wherein the first and second flow-rate transducers are differential pressure transducers.

19. The fluid flow-rate matching system of claim 18, wherein the first flow path is a water replacement flow path of a kidney dialysis machine, and wherein the second flow path is a waste water flow path of the kidney dialysis machine.

* * * * *